United States Patent [19]

Rowe

[11] 4,075,462
[45] Feb. 21, 1978

[54] PARTICLE ANALYZER APPARATUS EMPLOYING LIGHT-SENSITIVE ELECTRONIC DETECTOR ARRAY

[76] Inventor: William Guy Rowe, P.O. Box 425, Boonville, Calif. 95415

[21] Appl. No.: 539,341

[22] Filed: Jan. 8, 1975

[51] Int. Cl.² .......................................... G06M 11/00
[52] U.S. Cl. .............................. 235/92 PC; 235/92 V; 235/92 R; 250/222 PC
[58] Field of Search ........... 235/92 PC, 92 DP, 92 N, 235/92 V, 92 ME, 92 MT, 92 FL, 92 CT, 92 R; 340/146.3 Z, 146.3 AC, 146.3 MA; 250/222 PC; 356/102

[56] References Cited

U.S. PATENT DOCUMENTS

| | | | |
|---|---|---|---|
| 3,260,995 | 7/1966 | Hempel | 340/146.3 MA |
| 3,277,286 | 10/1966 | Preston, Jr. | 235/92 PC |
| 3,315,229 | 4/1967 | Smithline | 235/92 MS |
| 3,603,875 | 9/1971 | Coulter et al. | 235/92 PC |
| 3,676,647 | 7/1972 | Staffin et al. | 235/92 PC |
| 3,710,319 | 1/1973 | Miller et al. | 340/146.3 MA |
| 3,766,520 | 10/1973 | Patterson | 340/146.3 MA |
| 3,790,760 | 2/1974 | Stiller | 235/92 PC |
| 3,873,974 | 3/1975 | Bouton et al. | 340/146.3 AC |
| 3,941,982 | 3/1976 | Knollenberg et al. | 235/92 PC |

*Primary Examiner* — Joseph M. Thesz
*Attorney, Agent, or Firm* — Michael L. Harrison

[57] ABSTRACT

A particle analyzer system which operates on-line, real-time and is adaptable to use in process control systems wherein the analysis provides a basis for control of the process. Images of particles are focused onto an array of light sensitive electronic elements. The resulting light pattern is translated into digital data which is retrievably stored in a memory. Analysis of the data by digital logic yields information as to particle counts, size, shape and other physical characteristics. Interim storage in the light sensitive array itself is provided which allows data accumulation using short duration stroboscopic illumination.

11 Claims, 5 Drawing Figures

Fig_4

Fig_5

PARTICLE ANALYZER APPARATUS EMPLOYING LIGHT-SENSITIVE ELECTRONIC DETECTOR ARRAY

BACKGROUND OF THE INVENTION

The present invention relates to equipment for use in counting, sorting as to size and shape, and displaying in count, size and shape format the particle content of a fluid.

The need exists for apparatus capable of rapid analysis of particles, particularly particles suspended in a moving fluid. Applications for such apparatus are widespread and include such diverse fields as water and air pollution studies, ore refining, bacteriology, pathology, metallurgy, basic medical research and medical diagnosis.

While some applications are accommodated by using laboratory type instrumentation, a great many other applications require instruments which can operate on-line, in real-time so that the information gained from the analysis may be used in a process influencing manner to enhance the yield of the process.

In the past, assessment of the particle content of fluids has been accomplished by preparing for microscopy and analyzing a sample taken under controlled conditions. Photographs of precise enlargement may be taken of the sample and may be visually examined, or direct visual examination of the sample through the microscope may be used as well. A laboratory technician counts the number of particles and classifies them as to size in a representative and precisely known area of the sample. The process is tedious, time consuming and subject to wide variation according to the skill, acuity of vision and morale of the technician. These problems are further compounded when particles of a great range of sizes and shapes are present in the sample.

To overcome these disadvantages, systems have been devised which employ analog television cameras or discreet beam spot scanners both of which employ the principle of dividing a fixed field of view into a number of adjacent scan lines each of which represents a narrow slice of the field of view. By electronic timing and synchronization, the presence and location of particles in each line may be detected. Adjacent lines may then be electronically compared and the presence or absence of the image on each adjacent line determined. By measuring the time each particle is present in a single scan and by counting the number of successive scans in which the particle is present, a two-dimensional measurement of the particle is accomplished.

While a motionless sample may be scanned in this manner without difficulty, if the sample is in motion, as will occur for example in almost all process control applications, it will be appreciated that the problems of rendering unambiguous counts of particles and of determining the sizes and shapes of particles are increased considerably. Conventional television cameras typically have frame rates of 10 to 30 frames per second, and lines per frame of from 200 to 1000. As sample flow velocities become low with respect to the rate at which the line scan moves across the field, the tendency for duplicate counts to occur is increased. As the sample flow velocity becomes high and reaches an appreciable fraction of the line scan rate, the tendency to miss counts becomes greater. Furthermore, the counts of the smaller particles in a grouping will be missed more frequently than will be counts of the larger particles due to the lower probability of detection for the smaller particles. While rates of flow may be adjusted to within a narrow range by, for example, controlling dilution of the main sample, the ambiguity cannot be completely resolved. Furthermore, the skew in data which results from a varying probability of detection cannot be easily corrected by statistical manipulation since the particle distribution functions are typically rather irregular. Crude simplifying assumptions as to the behavior of the curve of the distribution function are required in order to make even rudimentary corrections.

Shape detection is also adversely affected by flowing samples. If the particle image velocity is such that its image crosses the image plane in the same direction and in the same time as the scan, the particle image will appear to be as long as the screen is high. An opposite effect, i.e. apparent shortening of the image, will occur if the motion is in an opposite direction. Using stroboscopic illumination of less than the frame completion time is of course impossible since only a portion of the scan would be illuminated. Therefore, illumination requirements and frame rates are always interrelated in analog television cameras. It will be readily apparent from this that "motion stopping" action by means of stroboscopic illumination is limited to particle velocities which traverse the field of view in times much greater than the time required for a complete frame scan.

While it might seem that increasing or decreasing scan rates would be desirable in order to accommodate increases or decreases in sample flow rates, the basic scheme of operation of analog television cameras precludes variation of scan rates in practical systems. This practical limitation results from the need for critical timing and synchronization of the system. To make useable the video output of the camera, the location of the scanning beam at which each increment of video output is produced must be precisely known. In order to know precisely this location, the exact timing of the beginning of the scan, the exact rate of the scan, and the exact position of each scanning line on the camera screen must be precisely known and controlled. In practical systems, the timing and scan rates are rigidly fixed and every effort is made to prevent them from varying. While it is theoretically possible to make such a system operate asynchronously, from a practical standpont this is not a sound approach since extreme complication in the design of all aspects of the system is the immediate result of attempts to make the system operate asynchronously.

An additional problem in analog television system is that the sensitivity of the system is related to the rate at which the beam sweeps the screen. Slower sweeps may be used to increase the sensitivity, but this reduces the maximum sample rate and limits the speed of sample flow which can be accommodated. Conversely, sample rates may be increased but at the expense of sensitivity. Thus, if either parameter is optimized, the other suffers proportionally.

Some of the sensitivity limitation may be overcome by using higher illumination levels when higher than normal frame rates are employed. A practical limitation on maximum useable illumination is quickly reached, however, since high intensity illumination brings into play size, weight and thermal dissipation considerations which make compact sample chamber designs impractical.

Errors are common to all scanning methods of particle analysis due to factors such as coincidence of particles, irregular shapes of particles and edge-scanning of particles. The customary method for handling these problems is to make a statistical adjustment in the output data. This method is usually satisfactory depending upon the precision required for a particular application. A more vexing problem, however, is the error due to the presence of bubbles in the sample. Bubbles may be present in all size ranges and are a particular concern when the sample is drawn from highly turbulent processes. A ball mill cyclone in the ore refining industry is a good example of such a sample source.

The bubble presents an unusually troublesome source of errors because its optical image appears essentially the same as a solid, spherical particle. The quantity of bubbles present in a sample is unpredictable and therefore statistical corrections are impossible. The analyzer must therefore be capable of distinguishing bubbles from solid particles in order to yield an accurate count. Some systems have attempted to avoid this problem by eliminating bubbles from the sample fluid. This approach is technically sound, but the apparatus which is required is bulky, heavy, and mechanically complex.

One property of the optical image of a bubble allows it to be distinguished from that of a solid particle if apparatus is available which is capable of pattern recognition. Most of the light which is incident upon the surface of a bubble is refracted away from its original path, leaving an apparent shadow, as would a solid particle. However, at the center of the bubble, light is perpendicular to the surfaces of the bubble and is therefore not refracted. Instead it passes through the bubble, giving the image of the bubble the appearance of a solid particle having a small aperture at the center.

Systems which rely on edge detection by a scanning beam are confounded by this shape. Since simple analog scanning systems do not store image data, it is impossible to perform even simple pattern recognition routines without resorting to elaborate analog storage and retrieval systems. On-line operation of such a system would be prohibitively slow, using known techniques, and would require conversion of analog data to a digital format for processing, thereby adding to the expense and complexity of the system.

SUMMARY OF THE PRESENT INVENTION

The principal object of the present invention is to provide a particle analyzer responsive to and capable of distinguishing between particles having a wide range of sizes and shapes, and capable of operation at speeds which render it useable on-line, real-time, in process control applications.

It is another object of the present invention to provide a particle analyzer which is capable of operation in conjunction with a moving sample with minimal count ambiguity or shape and size analysis error resulting from the sample motion.

Yet another object of the present invention is to provide a particle analyzer capable of determining and displaying the relative numerical distribution of various sizes and shapes of particles.

Briefly, in accordance with the present invention, particles are counted and analyzed by projecting a beam of light through a sample entraining fluid and by focusing an image of the particles onto an image plane in which there is located a large scale array of photosensitive electronic elements. Each element is addressed and read out in digital form and information so obtained is stored in a digital random access memory having the same word capacity as there are elements in the array. The information generated by the array and stored in the memory becomes the electronic equivalent of a microscope slide. The information contained in this "slide" is analyzed by a digital analysis process which counts the particles, classifies them as to sizes and stores the information thereby obtained.

In another feature of the present invention, the information stored in the digital processor is combined with flow rate information and the combination is analyzed to yield particle count per unit volume and, if desired, particle counts sorted as to size per unit volume or percentage of solids by weight.

In still another feature of the present invention, the relative particle distributions are determined and the information transferred into a continuously updated histogram display.

In yet still another feature of the present invention, the sample chamber light source comprises high intensity stroboscopic illumination of very short duration, whereby analysis of very rapidly moving particles is made possible due to the storage properties of the photosensitive array. In this feature, the information contained in the "slide" is retained in the photosensitive array for sufficient time to transfer the information to the random access memory where it is retrievably stored for processing. While memory cycle time and processing time is large compared to the duration of the stroboscopic illumination, the sampling rate is still rapid enough to detect statistical changes in particle content of the sample.

In yet another feature of the present invention, for those applications in which it is desirable to distinguish shapes of particles, a pattern recognition capability is provided which in addition to distinguishing shapes can eliminate false particle counts due to bubbles in the sample fluid.

DESCRIPTION OF PREFERRED EMBODIMENTS

Figures 1, 2:
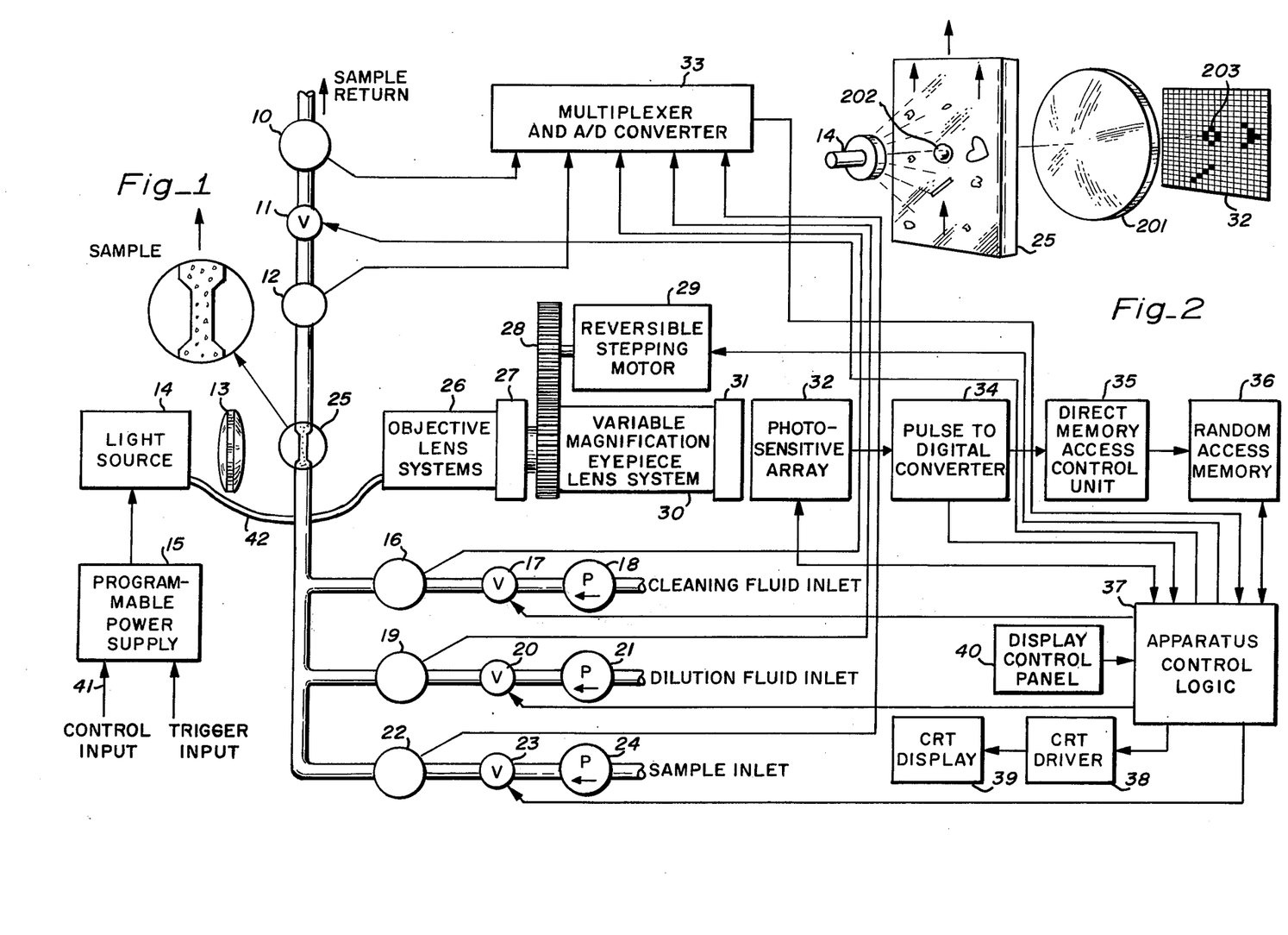
FIG. 1 is a schematic diagram, in block diagram form, depicting a particle analyzer incorporating the features of the present invention.
FIG. 2 is a diagram representing the illumination of the particle entraining sample as it passes through the sample chamber, the focusing of the transmitted light, and the resulting light patterns which are incident upon the array of the photosensitive electronic elements.

Referring now to FIG. 1, there is shown a particle analyzer incorporating features of the present invention. The particle analyzer includes a sample chamber 25 through which is passed a sample entraining fluid. The sample chamber is depicted as completely transparent for illustration purposes, but is preferably transparent only on two opposite sides, for transmitted light sample illumination. The sample chamber is also preferably designed in such a manner as to create turbulence, due to chamber geometry, which produces a random distribution and orientation of the particles as the sample passes through the sample chamber.

A fluid control system consisting of pumps 18, 21 and 24, and valves 17, 20 and 23 provides means for controlling the rate of flow of the sample fluid and its dilution, and for cleaning the sample chamber, as conditions require. Flow meters 10, 16, 19 and 22 are provided in each branch of the fluid control system for use in determining flow rates and dilutions. Adjustment of these quantities, or incorporation of their effects into statistical computations, is facilitated by the flow meters. A density gauge 12 is also provided in the output line for computation and display of percentage of solids by weight.

A light source 14 controlled by a programmable power supply 15 provides illumination of the sample fluid as it passes through the sample chamber.

Although illumination may be provided by any light beam sufficient to cover the viewing area with uniform illumination intensity, collimated light is preferred and is shown in the preferred embodiment as being accomplished by collimating lens 13. A monochromatic source of light such as a laser is also preferred since it significantly reduces the complexity of the optical system required to collimate the beam and to focus the image on the focal plane, as is well known. A laser also offers the possibility of pulsed operation at high intensities which affords higher speed sampling capability, as will be described. Furthermore, laser illumination may be chosen which is adapted to the optimum sensitivity wavelength of the silicon photodiodes which comprise the photosensitive array 32.

While transmitted light illumination is shown as the preferred embodiment, it is also possible to employ reflected light illumination and it will in some cases be desirable to do so.

Images of the particles in the sample are focused onto a focal plane by a variable magnification lens assembly comprising an objective lens system 26, a coupling ring 27, a variable magnification eyepiece 30, and its coupling ring 31.

Located in the focal plane of the focusing lens assembly is a large scale, e.g. 100 elements by 100 elements matrix array 32 of silicon photodiodes. Images of the sample particles are focused onto the array and, in the case of transmitted light, a shadow image of the particles results. FIG. 2 shows, in simplified diagrammatic form, the relationship between the light source 14, the sample chamber 25, the focusing lens 201, and the photosensitive array 32. Particular attention is directed to the bubble 202 inside the sample chamber 25 and the image of the bubble 203 on the array 32. The characteristic bright spot in the center of the bubble image 203 is used to distinguish bubbles from solid spherical particles.

Again referring to FIG. 1, the magnification of the lens assembly 26, 27, 30 and 31 is controlled by a reversible stepping motor 29 which adjusts the variable magnification eyepiece 30 over its range by means of a gear drive 28. Magnification of the particles is selected in accordance with the size range to be analyzed. Minimum size particles require magnification at least to the point at which the smallest image of interest covers an appreciable fraction of a photosensitive element. Further magnification until the smallest image of interest covers a 3 element section of the array, as a minimum, will be required before the analyzer's bubble elimination capability can be employed.

Figure 4:
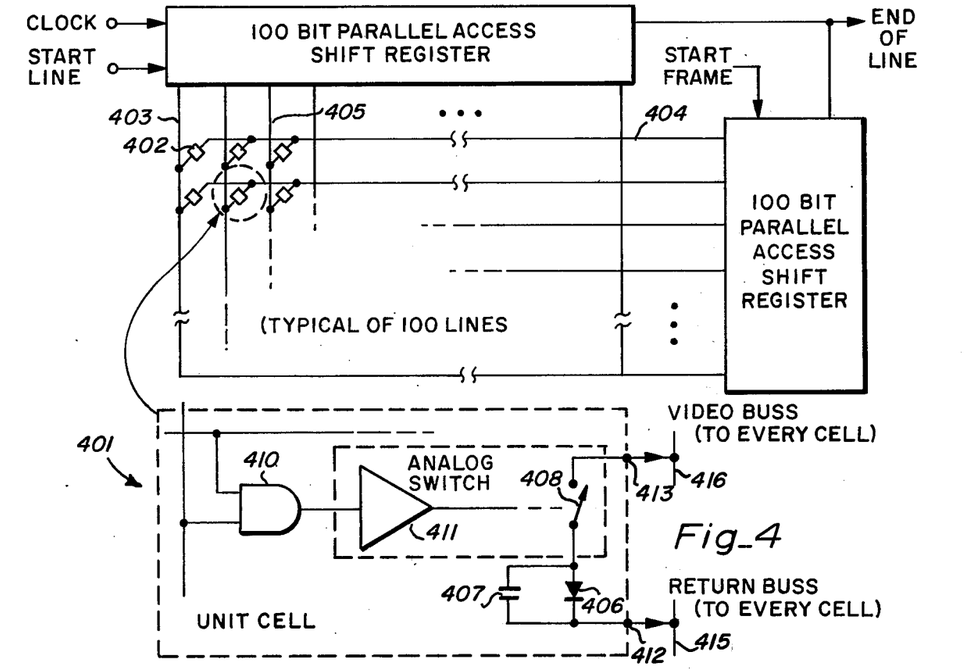
FIG. 4 is a schematic diagram, in partial block diagram form depicting the preferred embodiment of the array of photosensitive electronic elements.

FIG. 4 shows the preferred embodiment of the photosensitive array in simplified schematic form. A portion of the array is shown to simplify the drawing. A detail 401 of a unit cell 402 is also shown which is typical of all cells in the array. In the example shown, the array is organized into a two-dimensional matrix having one hundred rank lines 403 and one hundred file lines 404, or 10,000 intersection points 405 corresponding to 10,000 photosensitive elements. At each intersection point a unit cell 402 is located. In the detail of the unit cell 402 it may be seen that there are included a silicon photodiode 406, a capacitor 407 parallel connected to the silicon photodiode 406, an analog switch 408, an "AND" gate 410, and driver 411, driving the analog switch 408.

Each cell has two logic inputs which are connected to the "AND" gate 410, a return connection 412, and a video output 413. Each return is connected to a common return buss 415 and each video output 413 is connected to a video buss 416. Signal flow, through the video buss 416 and common 415 is controlled by the condition of the analog switch 408 which is in series with the common terminal 412, the video output terminal 413, and the photodiode 406 paralleled by the capacitor 407. The condition of the analog switch 408 is in turn controlled by the condition present at the logic inputs to the cell.

For each rank of the array, one input of each cell is connected to a common buss, while for each file of the array, the remaining input is connected to a common buss. Thus, it is possible to select any given cell by choosing and energizing the corresponding pair of rank and file common busses, thereby connecting the photodiode-capacitor combination 407 and 406 to the video buss through the analog switch 408. The selection rate is normally controlled at a fixed value so that the time of exposure to illumination is also controlled if continuous illumination is employed. As each cell 402 is selected, the capacitor 407 which parallels the photodiode 406 is connected to the video buss 416, and is charged to the potential difference which exists between the video buss 415 and the return buss 415. During the remainder of the cycle time, the photodiode's 406 photo current discharges the capacitor 407 at a rate dependent upon the illumination to which the diode 406 is exposed. In the absence of any illumination, no current flows through the diode 406, and the capacitor 407 remains fully charged. Selection of the same diode 406 repeatedly, under dark conditions, will not result in any signal flow on the video buss 416. However, if any illumination falls on the photodiode 406, the capacitor 407 will be discharged proportionally to the average intensity of the illumination. Connecting the unit cell 402 to the video buss 416 under this condition will result in a flow of charge into the capacitor 407 from the video buss 416. The current pulses created by this process are the output video of the array.

Figure 3:
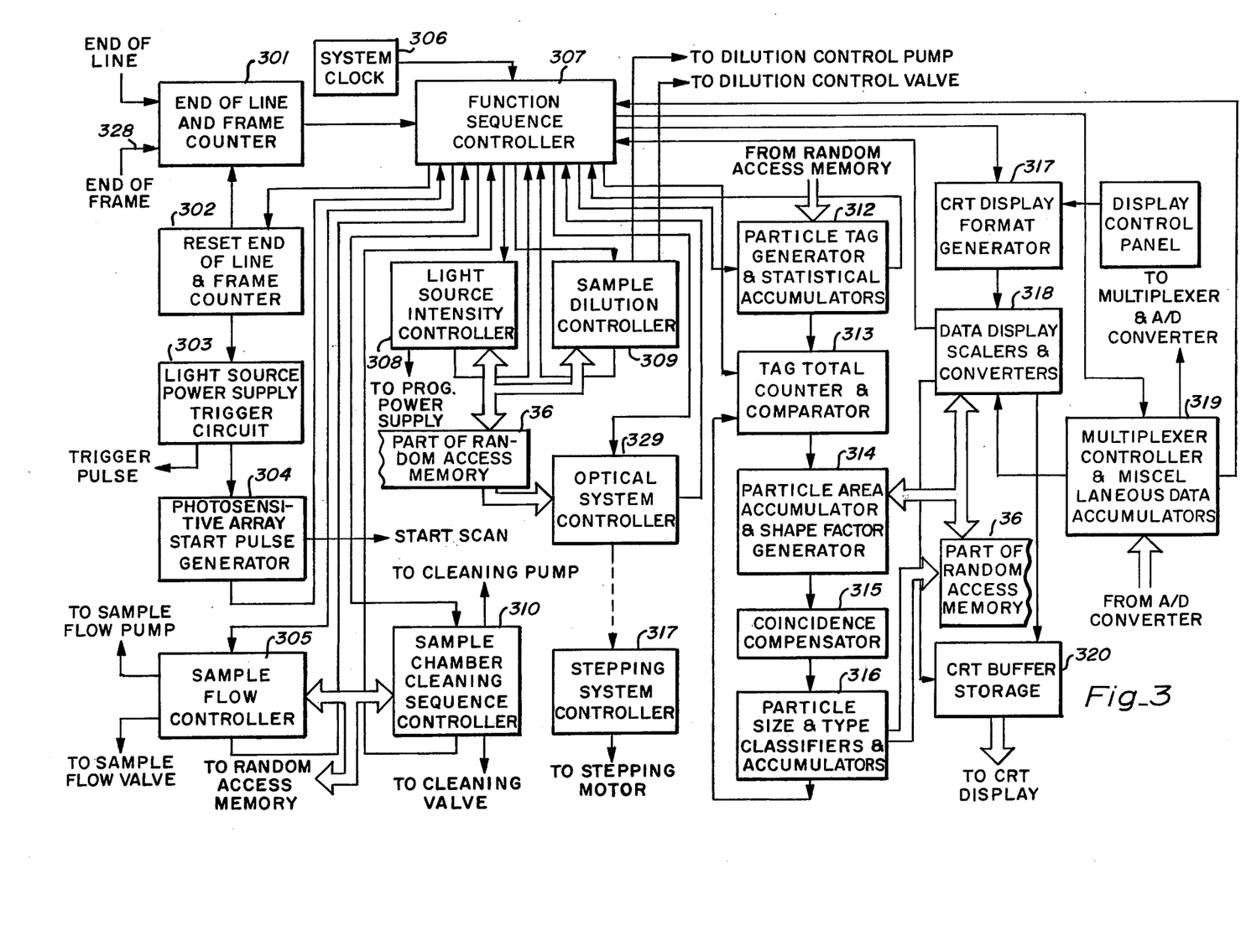
FIG. 3 is a detailed block diagram showing the constituent parts of the apparatus control logic portion of FIG. 1.

Selection of the diodes 406 in an orderly sequence is facilitated by providing two 100-bit parallel access shift registers 417 and 418 each of whose outputs drive one of the lines corresponding to rank and file logic busses respectively. At the start of a sequence, a start pulse from a photosensitive array start pulse generator 304 enters a bit into the start pulse input of, for example, the rank shift register 417. With each succeeding clock pulse, the bit advances down the register sequentially energizing each rank buss and thereby enabling one input of the gates of all of the unit cells 402 attached to that buss. If a similar bit is entered into the file register 418, and the file register bit is advanced by one position each time the rank register has been completely cycled, a sequential scan of every individual element of the array will be accomplished.

When continuous illumination is employed, operating the array in a charge storage, charge depletion mode takes full advantage of the diodes' inherent sensitivities since light current is integrated over virtually the entire cycle time of the array. When used with stroboscopic illumination, this advantage is lost, but is may be compensated for by use of higher instantaneous light intensities.

The illumination source is more complicated if stroboscopic illumination is employed, but the storage property of the array makes stroboscopic illumination desirable. By using stroboscopic sources of high intensity and short duration, "motion stopping" operation at speeds orders of magnitude higher than is currently possible in analog camera systems is possible. For example, light duration of as little as 200 nanoseconds may be employed. Within this time period a full frame of particle images can be recorded, corresponding to the entire frame scan of an analog television camera system. The image which impinges on the array is stored as a charge depletion in the capacitors which parallel each diode. Duration, intensity and lens opening may all be adjusted to yield a video output (charge restoration) signal equivalent to the optimum constant illumination video output, but without the imge skew which would result if the image were illuminated for the time required to scan the array.

The inherent image memory capability of the array therefore allows the system to be employed in high sample velocity applications without image distortion or count ambiguity resulting from the movement of the sample.

Distance measurement using the array differs markedly from the technique used in converting the output of an analog television camera into units of distance. In the array, the position of each source of video data is known without requiring that reference be made to frame rates, scanning rates or the timing of the beginning of each successive scan. Since sweep waveforms are not required, the linearity problems which plague analog systems are completely eliminated. Timing is non-critical since the processing of the video takes place independently of the data sampling process. If fact, fully asynchronous operation is readily achievable and may be the preferred mode of operation in applications where wide variations in sample flow rates occur.

The array is inherently compatible with digital processing techniques. Referring again to FIG. 1, outputs from the array are digitized by means of a pulse to digital converter 34 which renders all video pulses into digital words dependent upon the amplitude of the pulse. In systems in which grey scale information is not required, the conversion can be simplified to yield a two-state output in which presence of a particle image is represented by a "1" and absence is represented by a "0". For simplification, the preferred embodiment is described as a two-state light value system. Memory capacity requirements and cycling times are reduced proportionally as the image grey scale distinctions are reduced.

The location of each video source and consequently the location of each particle is known by the "0"- "1" pattern stored in the random access memory 36 and by the simple expedient of organizing the random access memory 36 into a two-dimensional format of rank and file equal in extent to those of the array, the same digital circuitry which drives the rank and file of the array may also be employed for locating and storing the video data from each element in a corresponding location in the memory.

Referring now to FIG. 3, further details of the apparatus control logic 37, and its relationship to the random access memory 36, of FIG. 1 are shown in simplified block diagram form. The logic required to accomplish the control, calculation, statistical analysis and display function may be realized by either hard-wired special purpose logic circuits, or by a programmed special purpose computer. The preferred embodiment is described generally so as to apply to both.

Logic functions are timed by a system clock 306 and are controlled as to sequence of operation, interruption priorities and sub-function sequencing by function sequence controller 307.

Three distinct although interrelated functions, accumulation, analysis and display of data are employed in analyzing particle samples. Five functions are employed in maintaining the sample fluid, the sample chamber and the optical system within the analyzer's desired operating ranges. It will be possible and desirable to eliminate some or all of these latter five functions in those applications which are characterized by narrow ranges of flow velocity, particle density and particle size. For completeness the preferred embodiment shows all of the functions which would be required for the most damanding applications.

Considering first the function of data accumulation, an end of line and frame counter 301 is responsive to pulses driving the rank and film registers of the array corresponding to the selection of each unit cell position in the array 32. Pulses corresponding to the clock pulses driving the rank shift register are indicative of which of the rank lines is being selected at any given instant. Likewise, pulses corresponding to the clock pulse input of the file shift register are indicative of which film line is being selected. By counting these pulse inputs, the end of each line and end of each frame are known, and in turn, the completion of data transfer from the array to a random access memory 36 is also known.

Since the number of pulses from the start of the scan is indicative of the position of the unit cell which produces the video output, storage of the image data in a random access memory 36 is facilitated. Special relationships among particles and particle dimensions are retained in storage in the random access memory 36 until an identifying tag has been added to each data group representing a particle.

Synchronization of the light source, required when stroboscopic illumination is employed, is provided by a light source power supply trigger circuit 303 which is responsive to an initiate data command from the function sequence controller 307. This circuit generates a precisely timed pulse which activates the light source power supply 15 causing the light source 14 to emit light for a period of time and at an intensity selected in accordance with the speed of flow and the turbidity of the sample.

Following the completion of the light pulse, a diode array start pulse generator 304 signals that new data is available from the array, and interrogation of the array begins, with the random access memory 36 receiving the stored data from the array, and continues until the end of frame signal received at input 328 indicates that all the data has been retrieved from the array and has been stored in the random access memory 36. Data accumulation is thereby completed for this data frame, and the analyzer is ready for another set of data to be accumulated by again strobing the light sources in response to a command from the function sequence controller 307.

Data analysis is initiated by the particle tag generator and statistical accumulator 312 in response to command from the function sequence controller 307. This circuit scans the data frame stored in the random access memory 36, and, upon detection of a data group representing a particle, assigns to such data group a unique identifying tag. The identifying tag is stored along with the data group in the random access memory 36. Thereafter, as the particle characteristics represented by the data group are determined, they are associated with the identifying tag and also stored in the random access memory 36.

For each particle associated with the tag identifiers, data representing the cross section of the particle, i.e. its image in silhouette, is available. From this data, by means of digital computation may be derived the maximum and minimum chords of the particle, its circumference, its area, and its approximate shape. By analyzing each image for presence of light at its center, bubbles in the sample may be detected and eliminated from the statistics.

In the limiting case, a data group may consist of the output of but one cell 402 of the array 32, corresponding to a particle image approximately the same area as the sensitive portion of one silicon photodiode 406. While this data group would be sufficient for registering the count of one particle, it contains no information as to the shape of the particle. For minimum pattern recognition and shape sorting to be accomplished, the image of the particle must overlap at least a three by three segment of the array 32, as previously described.

Areas of each particle are determined by a particle area accumulator and shape factor generator 314. Areas may be determined, due to the inherently metric properties of the array 32, by simply counting the number of adjacent unit cells and determining the areas represented by the total, consideration being given to the magnification factor which has been selected for the lens assembly, 26, 27, 30 and 31.

Particle shapes are identified and classified into selected categories by the particle area accumulator and shape factor generator 314. In many applications, it will be important to distinguish only two shapes, e.g. rock fragments may need to be distinguished from malleable materials. In such cases histogram displays of both shapes may be provided on the same cathode ray tube thus providing a quick comparison of relative distribution of both types of particles.

In all cases it is desirable to eliminate bubbles from the statistics. The pattern recognition capability of the analyzer provides a means for accomplishing that result as well as for sorting true particles into shapes.

Data associated with each tag having been characterized as to size or shape may then be sorted into ranges classified as to any of the selected characteristics, by the particle size and type classifiers and accumulator 316.

Small particles which are in line with larger particles between the light source 14 and the array 32 will not be registered as a data group, since their silhouettes are overlapped by the larger particles. In those situations in which it is important to register the count of smaller particles, the coincidence compensator 315 adds counts to the smaller count categories in proportion to the ratio which the area of the larger particles bears to the total sample area. This corrects, on an average basis, for errors which are due to the coincidence described.

The accumulated and classified data stored in the random access memory for each frame may be accessed by readout circuits directly, or may be further accumulated in a buffer memory for the purpose of averaging and formatting the data into, for example, a histogram display.

Many display types are useable with the particle analyzer. The preferred embodiment utilizes a cathode ray tube display 39 because it is readily varied to meet differing requirements, is capable of rapid changes in information and provides high information density. Selection of the type of display, the ranges, and the scale factors is accomplished in the preferred embodiment by a display control panel 42 which establishes inputs for a cathode ray tube display format generator 317.

The most meaningful data display is preferably based upon the analysis and statistical accumulation of a large number of frames of data. Once a number of frames have been analyzed, it is possible to determine the average of their statistics, and to display that average, whereas single frame of data may give a totally unrealistic assessment of the overall sample characteristics. After the average of a number of frames has been accumulated, the data may be continuously updated in accordance with the latest data frame by erasing the oldest data from the buffer memory and replacing it with data from the most recent data frame. Since one frame of data is added, and one frame is subtracted each time the data is refreshed, the displayed data always represents the accumulated and averaged data of the same number of frames thereby smoothing the statistical fluctuation which occurs from frame to frame.

Figure 5:
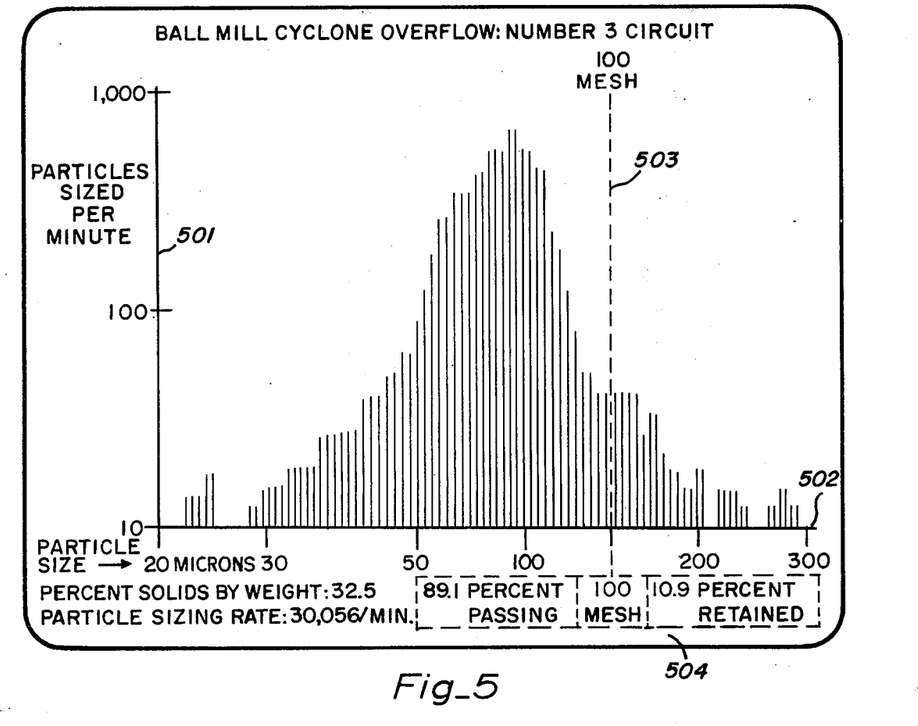
FIG. 5 is a diagrammatic depiction of a useful type of cathode ray tube display, typical of displays intended for ore refining applications, showing particle counts per unit time categorized in accordance to their size ranges.

A useful organization of the display is shown in FIG. 5. The vertical axis 501 represents quantity, and the horizontal axis 502 represents particle size. Since the process is continuous, the vertical axis is displayed not as a total quantity, but as quantity per unit time. In the application exemplified, it is important to know when particle sizes have been reduced to a particular size, or smaller. The ore refining industry characterizes particles in accordance with their ability to pass through a mesh of specified dimensions. The dotted vertical line 503 represents a specified mesh size. All particles represented by data to the left of the line will pass through such a mesh, while all particles represented by data to the right of the line would not. A simple arithmetic calculation based upon the stored data, may be used to compute the percentage retained by and the percentage passing through the mesh. This information is displayed in area 504.

Data based upon inputs from the flow meters and the densitometer may be used to calculate other statistics such as density and percent solids by weight. Numerical calculations of these statistics are performed by a data display scaler 318. Acquisition of flow rate and density data is accomplished by a multiplex controller and ancillary data accumulator 323.

In many applications, the analyzer can operate satisfactorily using sample flow rates which are determined by the origin of the sample fluid. In some applications, however, it is necessary to adjust sample flow rates to within the range which the analyzer can accommodate. Sample velocities are determined by a flow meter 10 whose output signal is received and converted into digital data by a multiplexer and analog to digital convertor 33. The digital data is compared with established limits stored in the random access memory 36 and if outside of the limits, a valve 23 and pump 24 are adjusted to either restrain or increase sample velocity as is required.

In some applications sample turbidity becomes so high that the photosensitive array receives little or no light, rendering the analyzer incapable of distinguishing between particles. The preferred embodiment employs a brightness control loop controlling light source intensity through control input 41, a dilution control pump 21 and a dilution control valve 20 which are employed to bring the image brightness within acceptable limits. A quantitative measure of sample turbidity is provided by comparing the intensity of the light transmitted through the sample with that of the light source itself as transmitted to the optical sensing system through light pipe 42.

A sample dilution controller 309 is responsive to image brightness data obtained from the array. If brightness is within an acceptable range, no adjustments are made in either brightness or dilution. However, if brightness at the image plane is below normal, the controller adapts to the below normal condition by first determining whether a brightness increase is possible. If the light source is operating at maximum output and no further increase can be accomplished, the controller adjusts dilution until the sample turbidity is low enough to produce an image of acceptable brightness. Failing to achieve either of these results, an alarm is activated notifying the operator that sample condition are beyond the range of the analyzer.

Depending upon the composition of the sample fluid, the sample chamber may suffer from deposits of material which reduce the image sharpness and contrast. A sample chamber cleaning sequence controller 310 is provided in the preferred embodiment which determines image contrast and sharpness by evaluating the abruptness of change in image intensities at the edge of the image. Lack of contrast and sharpness is noted, when present, and a sample chamber cleaning routine is initiated. A valve 17 and a pump 18 provide cleaning fluid through the cleaning fluid inlet which removes accumulated deposits from the sample chamber. During this operation, no data is recorded by the analyzer. Upon completion of the cleaning routine, data accumulation is again initiated. If the cleaning has not been sufficient to remove the deposits, an alarm is activated notifying the operator that sample chamber conditions are below the minimum acceptable.

The ratio of particle sizes which can be accurately analyzed using the described array is approximately 100 to 1. In principle, the invention may be carried out by using arrays of greater size having a greater number of elements, however, practical considerations make extension of minimum and maximum particle size range by changing optical elements more desirable. Accordingly, the preferred embodiment utilizes a variable magnification lens system 26, 29, 30 and 31 which is adjustably connected by a gear drive 28 to a stepping motor 29 which is responsive to the output of an optical system controller 328. Image data stored in the random access memory 36 is analyzed for its ability to resolve reticle lines scribed on the walls of the sample chamber. The dimensions of the reticle line image, as projected onto the array, are compared with the selected limits of particle size which the analyzer is to accommodate. If the reticle dimensions indicate that sufficient magnification is available to allow resolution of the smallest particle sizes which it is desired to analyze, no change is made. However, if the image size of the smallest particle would fall below the minimum required for analysis, the optical system controller will activate the stepping motor 29 causing an appropriate adjustment in lens magnification. A similar procedure is employed when the largest particle size which can be analyzed is the controlling consideration.

While one particular embodiment has been described, it will be appreciated that many variations of the particle analyzer may be practiced which fall within the scope of the present invention. A motionless sample may be desirable for certain laboratory applications, for example, and an almost limitless variation of the types of displays employed is possible. These various changes may be made by those skilled in the art without departing from the spirit of the invention.

What is claimed is:

1. An apparatus for acquiring and formatting digital data representative of size and shape characteristics of particles within a designated sample zone, comprising:
   a light source for illuminating, with coherent or incoherent radiation, the particles within the sample zone;
   a lens system for producing on a focal plane an image of the particles within the illuminated sample zone;
   a plurality of light-sensitive electronic elements located in the focal plane of the lens system having known and fixed spacings between the elements, each element having individually associated therewith memory means responsive to the light-sensitive elements for receiving and retrievably storing an analog of the total illumination incident upon each light sensitive element;
   interrogating means responsive to the memory means for individually sampling the analog of the total illumination level incident upon each light-sensitive electronics element; and,
   quantizing means for receiving each analog output from the interrogating means and converting each analog output into a digital data field representative of the illumination level incident upon each element of the array.

2. The apparatus of claim 1 wherein the lens system is a variable magnification lens.

3. The apparatus of claim 1 wherein the light source is monochromatic.

4. The apparatus of claim 1 wherein the light source is a laser.

5. The apparatus of claim 1 wherein the light source is a stroboscope.

6. The apparatus of claim 1 further including digital storage means for receiving and retrievably storing the digital data field.

7. The apparatus of claim 6 wherein the light source is a monochromatic.

8. The apparatus of claim 6 wherein the light source is a laser.

9. The apparatus of claim 6 wherein the light source is a stroboscope.

10. An apparatus for acquiring and formatting digital data representative of size and shape characteristics of particles contained in a fluent medium, comprising:
   a sample chamber having one or more transparent sides and having an inlet and an outlet;
   means for passing a sample of a particle-containing fluent medium of known dilution and known flow rate through the inlet and discharging it from the outlet of the sample chamber;
   a light source for illuminating the sample as it passes through the sample chamber;
   a lens system for producing an image of the illuminated sample respresentative of the size and shape the particles contained therein on a focal plane;
   a plurality of light-sensitive electronic elements located in the focal plane of the lens system having known and fixed spacings between the elements, each element having individually associated therewith memory means responsive to the light-sensitive elements for receiving and retrievably storing an analog of the total illumination incident upon each light sensitive element;
   interrogating means responsive to the memory means for individually sampling the analog of the total illumination level incident upon each light-sensitive electronic element; and,
   quantizing means for receiving each analog output from the interrogating means and converting each analog output into a digital data field representative of the illumination level incident upon each element of the array.

11. The apparatus of claim 10 further including digital storage means for receiving and retrievably storing the digital data field.

* * * * *